United States Patent [19]

Clinton

[11] 4,222,883
[45] Sep. 16, 1980

[54] 4,4'-FURFURYLIDENE BIS(2,6-DI-TERT-BUTYLPHENOL)ANTIOXIDANT

[75] Inventor: Ernest Clinton, Bloomfield Hills, Mich.

[73] Assignee: Ethyl Corporation, Richmond, Va.

[21] Appl. No.: 947,347

[22] Filed: Oct. 2, 1978

Related U.S. Application Data

[63] Continuation-in-part of Ser. No. 790,533, Apr. 25, 1977, abandoned.

[51] Int. Cl.$^2$ ............................................ C07F 307/42
[52] U.S. Cl. ................................... 252/52 R; 252/404; 260/45.8 A; 260/347.8; 260/398.5; 426/545
[58] Field of Search ............ 260/45.8 A, 347.8, 398.5; 252/52 R, 404; 426/545

[56] References Cited

U.S. PATENT DOCUMENTS

| | | | |
|---|---|---|---|
| 2,515,908 | 7/1950 | Stevens et al. | 252/52 R |
| 2,959,595 | 11/1960 | Beaver et al. | 260/332.3 R |
| 3,297,575 | 1/1967 | Worrel | 252/52 R |
| 3,812,152 | 5/1975 | Hofer et al. | 252/52 R X |

*Primary Examiner*—Richard Raymond
*Attorney, Agent, or Firm*—Donald L. Johnson; Robert A. Linn; Joseph D. Odenweller

[57] ABSTRACT

Organic material is effectively stabilized against oxidative degradation by adding a small amount of 4,4'-furfurylidene bis(2,6-di-tert-butylphenol).

4 Claims, No Drawings

4,4'-FURFURYLIDENE BIS(2,6-DI-TERT-BUTYLPHENOL) ANTIOXIDANT

CROSS REFERENCE TO RELATED APPLICATION

This application is a continuation-in-part of application Ser. No. 790,533, filed Apr. 25, 1977, now abandoned.

BACKGROUND

Many commonly used organic materials require antioxidant protection in order to extend their useful life. Such antioxidants prevent cracking, crazing and general degradation of organic compositions due to the effects of oxygen. Many phenolic compounds have been found to be useful as antioxidants. For example, 4,4'-methylene bis(2,6-di-tert-butylphenol) disclosed in U.S. Pat. No. 2,944,086 is a very effective antioxidant.

SUMMARY

According to the present invention a compound is provided which is a very effective antioxidant in a wide range of organic substrates. This new compound is 4,4'-furfurylidene bis(2,6-di-tert-butylphenol.

DESCRIPTION OF THE PREFERRED EMBODIMENTS

A preferred embodiment of the invention is an antioxidant compound having the formula

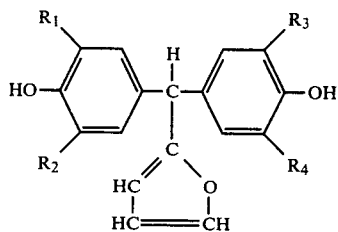

wherein $R_1$, $R_2$, $R_3$ and $R_4$ are tert-butyl groups, namely 4,4'-furfurylidene bis(2,6-di-tert-butylphenol).

The new compound of this invention can be made by reacting about 2 moles of 2,6-di-tert-butylphenol with about 1-2 moles of furfural in the presence of a basic catalyst (e.g. KOH) in a lower alkanol solvent (e.g. isopropanol) at reflux temperature. A satisfactory process is described in Filbey et al, U.S. Pat. No. 2,807,653, except that furfural is used in making the present compounds rather than formaldehyde.

The following example illustrate the preparation of the present compound.

EXAMPLE 1

In a reaction vessel was placed 400 ml ethanol, 6.6 g KOH, and 206 g 2,6-di-tert-butylphenol. While stirring at 30° C., 48 g of 2-furfurylidene was added over a 15-minute period and the mixture refluxed (82°–83° C.) for three hours. The mixture was cooled and after standing 65 hours, solids had precipitated. These were filtered off and washed with cold ethanol yielding 164 g crude product. An additional 57 g of solids was obtained by evaporating the filtrate. A portion of the crude product was recrystallized from ethanol followed by isooctane to yield 4,4'-furfurylidene bis(2,6-di-tert-butylphenol) (white solid, mp 158°–159° C., analysis 80.1% C, 9.25% H).

The 4,4'-furfurylidene bis(2,6-di-tert-butylphenol) is an effective stabilizer in a broad range of organic materials of the type normally subject to oxidative deterioration in the presence of oxygen during use over an extended period. In other words, the organic compositions protected by the present antioxidant are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additive is not a flame retarding additive nor flame suppressing additive and the degradation protected against is not combustion but, rather, the gradual deterioration of the organic composition due to the effects of oxygen over an extended period of time.

The amount of furfurylidene-bis-phenol added is a small antioxidant amount. A useful range is about 0.01–5 weight percent. A more preferred range is about 0.1–3 weight percent.

Examples of organic materials in which the additive is useful include polymers, both homopolymers and copolymers, of olefinically unsaturated monomers, for example, polyolefins such as polyethylene, polypropylene, polybutadiene, and the like. Also, poly-halohydrocarbons such as polyvinyl chloride, polychloroprene, polyvinylidene chloride, polyfluoro olefins, and the like, are afforded stabilization. The additive provides both antioxidant and antiozonant protection in natural and synthetic rubbers such as copolymers of olefinically unsaturated monomers including styrene-butadiene rubber (SBR rubber), ethylene-propylene copolymers, ethylene-propylene-diene terpolymers such as the terpolymer of ethylene, propylene and cyclopentadiene or cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrilebutadiene-styrene resins (ABS) are effectively stabilized. Ethylenevinyl acetate copolymers are protected, as are butene-methyl-acrylate copolymers. Nitrogen-containing polymers such as polyurethanes, nitrile rubber, and lauryl acrylate-vinylpyrrolidone copolymers are effectively stabilized. Adhesive compositions such as solutions of polychloroprene (neoprene) in toluene are protected.

Fats and oils of animal and vegetable origin are protected against gradual deterioration. Examples of these are lard, beef tallow, coconut oil, safflower oil, castor oil, babassu oil, cottonseed oil, corn oil, rapeseed oil, and the like.

Petroleum oils and waxes such as solvent-refined, midcontinent lubricating oil, microcrystalline wax, and Gulfcoast lubricating oils are effectively stabilized.

Animal feeds such as ground corn, cracked wheat, oats, wheat germ, alfalfa, and the like, are protected by mixing a small but effective amount of the present additive with these products. Vitamin extracts, especially the fat-soluble vitamins such as vitamin A, B, D, E and C, are effectively stabilized against degradation.

The additive is useful in foamed plastics such as expanded polystyrene, polyurethane foams, and the various foamed rubbers, alkyd resins such as short oil terephthalic acid-glycerol-linseed oil resins, and typical long oil resins of trimellitic acid-glycol-tung oil resins including epoxide-modified alkyl resins. Epoxy resins themselves such as isopropylidenebisphenolepichlorohydrin epoxy resins are stabilized against degradation.

Hydrocarbons such as gasoline, kerosene, diesel fuel, fuel oil, furnace oil, and jet fuel are effectively protected. Likewise, synthetic hydrocarbon lubricants, for example, $C_{6-12}$ α-olefin oligomers such as α-decene trimer are made very stable. Likewise, polybutene lubricants, di- and tri-$C_{12-30}$ alkylated benzene and naphthalene synthetic lubricants are protected.

Organometallics such as tetraethyllead, tetramethyllead, tetravinyllead, ferrocene, methyl ferrocene, cyclopentadienyl manganese tricarbonyl, methyl cyclopentadienyl manganese tricarbonyl, cyclopentadienyl nickel nitrosyl, and the like, are effectively protected against oxidative degradation. Silicone oils and greases are also protected.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ alliphatic monocarboxylic esters of pentaerythritol, complex esters formed by condensing under esterifying conditions mixtures of polyols, polycarboxylic acids and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyrridine catalyst are stabilized. Polycarbonate plastics and other polyformaldehydes are also protected.

Linear polyesters such as phthalic anhydride-glycol condensates are given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with other olefinically unsaturated monomers such as methylmethacrylates are also effectively stabilized.

The additive can be used to protect any of the many organic substrates to which an antioxidant is normally added. It can be used where economics permit to protect such substrates as asphalt, paper, fluorocarbons such as teflon, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethylsilicone lubricants, phosphate lubricants such as tricresylphosphate, and the like.

The additive is incorporated into the organic substrate in a small but effective amount so as to provide the required antioxidant protection. A useful range is from about 0.01 to about 5 weight percent, and a preferred range is from about 0.1 to 3 weight percent.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rebbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized. The following will serve to illustrate the manner in which the additives are blended with various organic substrates. The following describes organic compositions containing the additive of the present invention. In Examples 2–16 "additive" refers to 4,4'-furylidene bis(2,6-di-tert-butylphenol).

EXAMPLE 2

To a synthetic rubber master batch comprising 100 parts of SBR rubber having an average molecular weight of 60,000, 50 parts of mixed zinc propionate stearate, 50 parts carbon black, 5 parts road tar, 2 parts sulfur and 1.5 parts of mercapto benzothiazole is added 1.5 parts of additive. After mastication, the resultant master batch is cured for 60 minutes using 45 psi steam pressure, resulting in a stabilized SBR vulcanizate.

EXAMPLE 3

A synthetic SBR polymer is prepared by polymerizing 60 percent styrene and 40 percent butadiene in an aqueous emulsion employing a sodium oleate emulsifier and a peroxide catalyst. Following this, sufficient additive is added to produce 0.3 weight percent, based upon the SBR polymer. The emulsion is then coagulated using an acidified salt solution and the coagulated polymer compressed into bales for storage. The polymer is stable during storage and can later be compounded to prepare SBR vulcanizates.

EXAMPLE 4

One part of additive is blended with 100 parts of raw butyl rubber prepared by the copolymerization of 90 percent isobutylene and 10 percent isoprene, resulting in a stable elastomer.

EXAMPLE 5

A cis-polybutadiene polymer is prepared having 90 percent cis configuration by polymerizing butadiene in a toluene solvent employing a diethyl aluminum chloride-colbalt iodide catalyst. Following the polymerization, a small amount sufficient to provide 0.2 weight percent of additive is added to the toluene solution, following which the solution is injected into boiling water together with steam causing the solvent to distill out and the cis-polybutadiene to coagulate, forming a rubber crumb. The crumb is dried and compressed into bales, resulting in a stabilized cis-polybutadiene.

EXAMPLE 6

A butadiene-acrylonitrile copolymer is prepared from 1,3-butadiene and 32 percent of acrylonitrile. One percent, based on the weight of polymer, of additive is added as an emulsion in a sodium oleate solution. The latex is coagulated and the coagulum is washed and dried, resulting in a stabilized butadiene-acrylonritrile copolymer.

EXAMPLE 7

To 1,000 parts of a solid polypropylene powder is added 5 parts of additive and 10 parts of dilaurylthiodipropionate. The mixture is heated to its melting point and rapidly stirred and extruded to form a useful polypropylene filament.

EXAMPLE 8

To 1,000 parts of polyethylene is added 3 parts of additive and 5 parts of dilaurylthiodipropionate. The mixture is heated to its melting point and stirred and then passed through an extruder having a central mandrel to form tubular polyethylene which is inflated to form a useful polyethylene film.

EXAMPLE 9

To 100,000 parts of a midcontinent, solvent-refined, mineral oil having a viscosity at 100° F. of 373.8 SUS and at 210° F. of 58.4 SUS is added 500 parts of additive. Following this is added 100 parts of a zinc dialkyldithiophosphate, 50 parts of an overbased calcium alkaryl sulfonate, 1,000 parts of a poly dodecylmethacrylate V.I. improver and 2,000 parts of a 70 percent active oil solution of an alkenyl succinimide of tetraethylenepentamine in which the alkenyl group has a molecular weight of 950. The resultant mixture is blended while warm, following which it is filtered and packaged, giving a stable lubricating oil useful in automotive engines.

EXAMPLE 10

To 10,000 parts of a dimethyl silicone lubricating oil is added 50 parts of additive. The mixture is stirred at 50° C. until thoroughly blended, resulting in a stable silicone lubricating oil.

EXAMPLE 11

To 10,000 parts of corn oil is added 15 parts of additive. The mixture is stirred, giving a corn oil highly resistant to normal oxidative degradation.

EXAMPLE 12

To 10,000 parts of trimethylolpropane tripelargonate is added 200 parts of tricresylphosphate, 10 parts of dimethyl silicone, 10 parts of benzothiazole, 50 parts of phenyl-$\beta$-naphthyl amine, and 50 parts of additive, resulting in a stabilized synthetic ester lubricant.

EXAMPLE 13

Wax paper is made by impregnating paper with paraffin wax containing 0.05 weight percent of a mixture of additive. The wax paper is used to make containers for potato chips which results in chips having extended shelf life.

EXAMPLE 14

To 10,000 parts of gasoline having an 87 R.O.N. is added 20 parts of additive and sufficient commercial tetraethyllead antiknock fluid to provide 2.5 grams of lead per gallon, resulting in a stabilized gasoline having a 96 R.O.N

EXAMPLE 15

To 10,000 parts of 41 cetane diesel fuel is added 50 parts of hexyl nitrate and 25 parts of additive, providing a stable diesel fuel.

EXAMPLE 16

To 10,000 parts of melted lard is added 10 parts of additive and the mixture is stirred until thoroughly blended, resulting in a lard highly resistant to normal oxidative degradation.

From the foregoing, it is apparent how to prepare stable organic compositions using the additive of this invention.

The antioxidant of this invention may be used alone as the sole antioxidant or may be used in combination with other antioxidants or compounds which synergistically affect the effectiveness of the antioxidant. Examples of other antioxidants include 4,4'-methylenebis(2,6-di-tert-butylphenol), 1,3,5-trimethyl-2,4,6-tri(3,5-di-tert-butyl-4-hydroxybenzyl)benzene, 2,6-dicyclopentyl-4-methylphenol, 4,4'-thiobis(6-tert-butyl-m-cresol), 4,4'-butylidenebis(6-tert-butyl-m-cresol) $\beta$-(3,5-di-tert-butyl-4-hydroxyphenol) propionic acid pentaerythritol ester and the like.

Particularly preferred synergists are the dialkylthiodipropionates such as dilauryl-thio-dipropionate and distearyl-thio-dipropionate. Such synergists are particularly effective in polyolefin (e.g., polypropylene) compositions and are used in concentrations of about 0.05 to about 0.3 weight percent.

Other synergists are dialkyl phosphites (e.g., dibutylphosphite, trialkylphosphites (e.g., tributylphosphite), dialkyl tin sulfides (e.g., dibutyl tin sulfides) and the like.

Tests were conducted to demonstrate the antioxidant effectiveness of the additive. In one such test called a Polyveriform test, 1 weight percent of 4,4'-furfurylidenebis(2,6-di-tert-butylphenol) was dissolved in a solvent-refined mineral oil containing 0.05% iron oxide as iron-2-ethylhexoate and 0.1% lead bromide as oxidation catalysts. Air was bubbled through the oil at 300° F. for 20 hours following which the acid number and viscosity of the oil was determined. The following table gives the results obtained in this test compared to the non-additive oil.

| Additive | Acid No. | Percent Visc. Increase |
|---|---|---|
| none | 6.4 | 92 |
| 4,4'-furfurylidenebis-(2,6-di-tert-butylphenol) | 3.8 | 38 |

These results show that the additive is an effective antioxidant.

Further tests were conducted to compare the claimed compound with the prior art compounds. The following examples show the preparation of certain prior art compositions disclosed in Stevens et al, U.S. Pat. No. 2,515,908.

EXAMPLE 17

In a reaction vessel containing dry benzene and absolute ethanol was placed 0.68 g sodium. After the sodium had reacted the benzene and excess ethanol were evaporated off and the residue held under vacuum (15 mm abs.) at 110°-120° C. for 2 hours. Then 24 g of furfural and 82.1 g (0.5 m) of o-tert-butyl-p-cresol was added to the sodium ethoxide residue under nitrogen. This mixture was stirred and heated to 98°-102° C. It was stirred for 5 hours at 98°-102° C. The resultant product was dissolved in 500 ml hexane and the solution washed with water until neutral (4×250 ml each). The hexane solution was then extracted with 75% aqueous ethanol to remove any unreacted o-tert-butyl-p-cresol. Hexane was evaporated under vacuum leaving the product as described in Stevens et al.

EXAMPLE 18

A second prior art composition was made following the procedure of Example 17 except substituting 103.16 g. (0.5 mol) of 2,4-di-tert-butylphenol in place of the o-tert-butyl-p-cresol.

Tests were conducted to compare the prior art composition to that of the present invention. The first test was carried out by dissolving 1 wt.% of the test additives in mineral oil. The oil was placed in a cell containing a weighed copper-lead bearing. The test oil was heated to 175° C. and air was bubbled through it at 48 l./hr. for 72 hours. Test criteria were bearing weight loss, acid number, and percent viscosity increase. The following results were obtained:

| Additive | Bearing Wt. Loss (mg) | Acid No. | Viscosity Increase (%) |
|---|---|---|---|
| None | 551 | 15.4 | * |
| Example 17 | 4.1 | 10.0 | 220 |
| Example 18 | 37.4 | 11.5 | 237 |
| This Invention | 10.3 | 8.6 | 173 |

The results showed a significant improvement in acid number and viscosity increase. It was considered that the test conditions were too severe to clearly distinguish the effectiveness of the different additives. Therefore, the test was repeated at 150° C. acid number and viscosity increase were measured at 40, 72 and 96 hours and bearing weight loss measured at end of test. The following results were obtained:

| Additive | Bearing Wt. Loss (mg) | Test at 150° C. Acid Number | | | Viscosity Increase | | |
|---|---|---|---|---|---|---|---|
| | | 40 hrs. | 72 hrs. | 96 hrs. | 40 hrs. | 72 hrs. | 96 hrs. |
| None | 542.5 | 6.2 | 10.6 | 13.8 | 49.8 | 141 | 393 |
| Example 17 | 15.5 | 4.0 | 5.1 | 6.2 | 52.4 | 80.2 | 49.2 |
| Example 18 | 50.0 | 4.5 | 5.4 | 5.6 | 52.1 | 81.2 | 73.2 |
| This invention | 5.9 | 0.4 | 0.7 | 1.5 | 7.0 | 12.7 | 20.4 |

The results better differentiate the additives and show the marked superiority of the additives of this invention over that made following U.S. Pat. No. 2,515,908.

A further test was conducted in a synthetic α-olefin oligomer comprising mainly α-decene trimer and tetramer. This test was at 350° F. for 48 hours, additive concentration was 0.5%. The following results were obtained:

| Additive | Bearing Wt. Loss (mg) | Acid No. | Viscosity Increase % |
|---|---|---|---|
| None | 703 | 15.4 | 1818 |
| 4,4'Furfurylidene-bis(2,6-di-tert-butylphenol | 0.2 | 0.4 | 6 |

These results show that 4,4'-fufurylidenebis(2,6-di-tert-butylphenol) is extremely effective in stabilizing α-olefin oligomer synthetic lubricants against high temperature oxidation.

I claim:
1. The antioxidant compound 4,4'-furfurylidene bis(2,6-di-tert-butylphenol).
2. A lubricating oil composition containing an antioxidant amount of the compound of claim 1.
3. A composition of claim 2 wherein said lubricating oil is an olefin oligomer of lubricating viscosity.
4. A composition of claim 3 wherein said olefin oligomer is mainly a mixture of α-decene trimer and tetramer.

* * * * *